(12) United States Patent
Porée

(10) Patent No.: US 11,844,897 B2
(45) Date of Patent: Dec. 19, 2023

(54) ADJUSTABLE TUBE FOR INHALATION CHAMBER SHUNTING AND USE THEREOF IN MECHANICAL-VENTILATION CIRCUIT

(71) Applicant: PROTECSOM AMÉRIQUE DU NORD INC., Drummondville (CA)

(72) Inventor: Thierry Porée, Saint-Pierre-Eglise (FR)

(73) Assignee: PROTECSOM AMÉRIQUE DU NORD INC., Drummondville (CA)

( * ) Notice: Subject to any disclaimer, the term of this patent is extended or adjusted under 35 U.S.C. 154(b) by 786 days.

(21) Appl. No.: 16/663,877

(22) Filed: Oct. 25, 2019

(65) Prior Publication Data

US 2020/0054844 A1 Feb. 20, 2020

Related U.S. Application Data

(63) Continuation-in-part of application No. PCT/CA2018/050488, filed on Apr. 26, 2018.

(60) Provisional application No. 62/490,095, filed on Apr. 26, 2017.

(51) Int. Cl.
*A61M 15/00* (2006.01)
*A61M 16/08* (2006.01)

(52) U.S. Cl.
CPC ...... *A61M 15/0086* (2013.01); *A61M 15/002* (2014.02); *A61M 15/009* (2013.01); *A61M 15/0065* (2013.01); *A61M 16/0875* (2013.01)

(58) Field of Classification Search
CPC ........ A61M 11/00–08; A61M 15/0086; A61M 15/002; A61M 15/0065; A61M 15/009; A61M 16/0875; A61M 16/021; A61M 16/0883; A61M 16/0833; A61M 39/08; A61M 16/0816; A61M 16/14
See application file for complete search history.

(56) References Cited

U.S. PATENT DOCUMENTS 3,913,607 A * 10/1975 Price .................. A61M 16/127
                                                         431/114
4,938,210 A    7/1990 Shene
2010/0126502 A1 5/2010 Fink et al.
(Continued)

FOREIGN PATENT DOCUMENTS

GB    2412325      9/2005
WO    0183011      11/2001
WO    2013037759   3/2003

*Primary Examiner* — Elliot S Ruddie
(74) *Attorney, Agent, or Firm* — BENOIT & COTE INC.; Mathieu Miron

(57) ABSTRACT

There is described a method for operating an inhalation chamber. A duct in the inhalation chamber extends from an opening for a source of gas to an opening for patient output, the duct comprising two portions, of which the shapes are complementary to form the duct, and displaceable in relation with each other. A MDI (or pMDI) and/or a nebulizer are connected to the inhalation chamber. A relative displacement is made between the two portions of the duct to close the duct and shunt the dead volume of the inhalation chamber, making a direct passage from the source of gas to the patient. If the nebulizer or the MDI is connected, a relative displacement is made between the two portions of the duct to open the duct to an inner volume of the inhalation chamber where the nebulizer or the MDI is dispensing aerosol. Other configurations are possible.

8 Claims, 12 Drawing Sheets

(56) References Cited

U.S. PATENT DOCUMENTS

2011/0082380 A1\* 4/2011 Breen ............... A61M 16/0866
  128/203.12
2013/0081617 A1   4/2013 Cavendish
2014/0338662 A1\* 11/2014 Vecellio-None .... A61M 16/021
  128/200.23

\* cited by examiner

ADJUSTABLE TUBE FOR INHALATION CHAMBER SHUNTING AND USE THEREOF IN MECHANICAL-VENTILATION CIRCUIT

CROSS-REFERENCE TO RELATED APPLICATIONS

This application is a Continuation-in-Part of PCT/CA2018/050488, filed 26 Apr. 2018, which claims priority and the benefit of U.S. provisional patent application 62/490,095, filed Apr. 26, 2017, the specifications of which are hereby incorporated herein by reference in their entireties.

BACKGROUND

(a) Field

The subject matter disclosed generally relates to inhalation chambers, or spacers, for metered dose inhalers or nebulizers. More specifically, it relates to a tube making the inhalation chamber more adaptable to circumstances.

(b) Related Prior Art

Inhalation chambers are often used to administer aerosol drug. In the context of mechanical ventilation, aerosol drug delivery is used increasingly as a route of administration, especially for patients suffering from chronic obstructive pulmonary disease (COPD), asthma or chronic obstructive respiratory failure. For example, bronchodilators are drugs which are prescribed as aerosol during mechanical ventilation. Other drug classes are administered as aerosol. As such, high-dose antibiotics are a new area of research in the treatment of serious pulmonary infections. Mechanical ventilation creates a particular situation for generating and transporting aerosol in order to reach lung parenchyma.

In a MDI (Metered Dose Inhaler) or pMDI (pressurized Metered Dose Inhaler), the medicine is in a liquid suspension that can be pressurized using a propulsion gas. Inhalers are possibly the system for generating aerosol that is the best suited to administer drugs such as beta 2 adrenergic agonists or anticholinergics in mechanical ventilation when treating obstructive syndromes. A drawback of using inhalers is the necessity of synchronizing administration of the aerosol and inhalation of the patient. In mechanical ventilation, synchronizing administration must be done with the first phase of the respiratory cycle too. Using an inhalation chamber improves performance of the inhaler.

Inhalation chambers, or spacers, work as braking volumes in which particles ejected from the inhaler can slow down under friction with the air present therein. There is a four- to six-fold increase in lung deposition using an inhalation chamber, compared to when none is used.

Nebulizers are interesting in that they can be used to administer a variety of liquid drugs, not only bronchodilators, but also drugs that are not available for inhalers, such as antibiotics. Among the various types of nebulizers currently on the market, vibrating mesh nebulizers are known as the most efficient. This is a new generation of nebulizers designed for mechanical ventilation. This nebulizer allows nebulizing the whole volume that is introduced in the reservoir with no substantial increase of the solution temperature. Being ergonomic and compact, it is among the preferred nebulizing systems in mechanical ventilation.

It has been found that an inhalation chamber combining the input of a pressurized metered-dose inhaler (pMDI) and the input of a nebulizer is advantageous in many regards. Such as configuration is described below, and has been described in WO 2013/037759, incorporated herein by reference.

SUMMARY

According to a first aspect of the invention, there is provided a tube for an inhalation chamber, the tube having a longitudinal axis and comprising:
 a first tube portion having a first base with a cylinder shape and a first part-of-cylinder portion extending from the first base;
 a second tube portion having a second base with a cylinder shape and a second part-of-cylinder portion extending from the second base, the second part-of-cylinder portion being complementary and slidably mating with the first part-of-cylinder portion, the second base being aligned with the first base about the longitudinal axis, the second tube portion being rotatable with respect to the longitudinal axis of the tube to allow the second part-of-cylinder portion to cover different azimuth angles with respect to the first part-of-cylinder portion and thereby open or close the tube between the first base and the second base.

According to another aspect of the invention, there is provided an inhalation chamber comprising the said tube extending between a gas source opening and a patient output opening of the inhalation chamber, the inhalation chamber comprising at least one opening for dispensing aerosol into the tube.

According to an embodiment of the invention, there are further provided at least two openings for dispensing aerosol, one of the at least two openings located away from the tube, the other one of the at least two openings being located between the tube and the one of the at least two openings located away from the tube.

According to an embodiment of the invention, the one of the at least two openings located away from the tube is an opening for a metered-dose inhaler and the other one of the at least two openings is an opening for a nebulizer.

According to an embodiment of the invention, at least one of the first base and the second base extends outside of the inhalation chamber to be accessible to the user to slide to open or close the tube between the first base and the second base.

According to an embodiment of the invention, there are further provided at least two openings for dispensing aerosol, one of the at least two openings located at the gas source opening, one of the at least two openings not located at the gas source opening or at the patient output opening.

According to an embodiment of the invention, the at least two openings for dispensing aerosol comprise:
 an opening for a nebulizer provided by a surface of the inhalation chamber, and
 an opening for a metered-dose inhaler, the first base being secured into the entry opening of the inhalation chamber and having an opening aligned with the opening for the metered-dose inhaler of the inhalation chamber.

According to an embodiment of the invention, the inhalation chamber comprises a slot along the surface or an edge of the surface, and the second tube portion comprises a protrusion extending to the slot or the edge of the surface of the inhalation chamber.

According to an embodiment of the invention, the protrusion is a ring that is rotatable by a user.

According to an embodiment of the invention, the ring is provided at an edge of the mating surface and thereby also at the edge of the surface of the inhalation chamber.

According to an embodiment of the invention, the protrusion comprises a cone surface which forms a wall of the inhalation chamber.

According to an embodiment of the invention, the protrusion comprises a mating surface which mates with a first portion of the inhalation chamber that comprises the opening for the metered-dose inhaler and the opening for the nebulizer, thus completely forming the inhalation chamber.

According to another aspect of the invention, there is provided a duct for an inhalation chamber, the duct extending through an inner volume of the inhalation chamber and comprising:
a first portion having a first shape;
a second portion having a second shape complementary with the first shape to form a closed duct, the second portion slidably mating with the first portion;
the second portion being slidable by a user to open the closed duct by forming a window at a surface of the duct, the window opening on the inner volume of the inhalation chamber.

According to an embodiment of the invention, the second portion extends outside of the inhalation chamber to be accessible to the user to slide.

According to an embodiment of the invention, the second portion comprises a protrusion extending at least at a surface of the inhalation chamber to make the protrusion accessible to the user.

According to an embodiment of the invention, the protrusion is a ring.

According to an embodiment of the invention, the duct is a cylinder when closed.

According to an embodiment of the invention, the first shape of the first portion is a half-cylinder, and the second shape of the second portion is a half-cylinder, thus making the first shape and the second shapes complementary to form the cylinder.

According to an embodiment of the invention, the first shape of the first portion is a plurality of covers defining a plurality of windows, and the second shape of the second portion is a plurality of covers corresponding to the plurality of windows, thus making the first shape and the second shapes complementary to form the cylinder.

According to another aspect of the invention, there is provided an inhalation chamber comprising said duct, according to various embodiments, extending between an opening for a gas source and an opening for patient output of the inhalation chamber.

According to another aspect of the invention, there is provided a use of said tube (in an inhalation chamber), or said inhalation chamber, or said duct (in an inhalation chamber), according to various embodiments, in an inhalation treatment of a patient in need thereof.

According to another aspect of the invention, said tube, or said inhalation chamber, or said duct, according to various embodiments, is for use in an inhalation treatment of a patient in need thereof.

According to another aspect of the invention, there is provided a method of administering an inhalation treatment to a subject in need thereof comprising administering said inhalation treatment with said tube, or said inhalation chamber, or said duct, according to various embodiments.

According to another aspect of the invention, there is provided a method for operating an inhalation chamber comprising:

providing a duct in the inhalation chamber extending from an opening for a source of gas to an opening for patient output, the duct comprising two portions, each having a shape, the shapes being complementary to form the duct, and displaceable in relation with each other;
connecting to the inhalation chamber one of:
a first aerosol dispenser at a first aerosol dispenser input on the inhalation chamber; and
making a relative displacement between the two portions of the duct to close the duct to by-pass an inner volume of the inhalation chamber; and
making a relative displacement between the two portions of the duct to open the duct toward the inner volume of the inhalation.

According to an embodiment of the invention, making the relative displacement between the two portions of the duct to close the duct or to open the duct comprises rotating one of the two portions with respect to the other one of the two portions.

According to an embodiment of the invention, rotating one of the two portions with respect to the other one of the two portions comprises providing the duct with at least one of said two portions extending outside the inhalation chamber for rotating the one of the two portions with respect to the other one of the two portions by direct manipulation of the at least one of said two portions extending outside the inhalation chamber.

According to an embodiment of the invention, the first aerosol dispenser is a metered-dose inhalator and the first aerosol dispenser input is opposite the duct in the inhalation chamber.

According to an embodiment of the invention, the first aerosol dispenser is a metered-dose inhalator and the first aerosol dispenser input is adjacent the opening for the gas source and inside the duct.

According to an embodiment of the invention, there is further provided the step of providing a slot along a surface of the inhalation chamber that extends perpendicularly to a longitudinal axis of the duct, one of the two portions of the duct having a protrusion extending outwardly to the slot.

According to an embodiment of the invention, rotating one of the two portions with respect to the other one of the two portions comprises moving the protrusion extending to the slot along the slot.

According to an embodiment of the invention, there is further provided the step of providing an edge of a surface of the inhalation chamber that extends perpendicularly to a longitudinal axis of the duct, one of the two portions of the duct having a protrusion extending outwardly to the edge.

According to an embodiment of the invention, rotating one of the two portions with respect to the other one of the two portions comprises moving the protrusion extending to the edge along the edge.

According to an embodiment of the invention, the first aerosol dispenser is a metered-dose inhaler and the second aerosol dispenser is a nebulizer.

According to another aspect of the invention, there is provided a method for operating an inhalation chamber comprising:
providing a duct in the inhalation chamber extending from a gas stream opening to a patient output, the duct comprising two portions, each having a shape, the shapes being complementary to form the duct, and displaceable in relation with each other;
connecting to the inhalation chamber a first aerosol dispenser; and making a relative displacement between the two portions of the duct to close the duct or open the duct to modify aerosol transfer between the inhalation chamber and the duct.

As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

It has been found that the inhalation chamber, for example that of WO 2013/037759, may be too voluminous if it is placed after the Y shaped piece. In this case, the patient will have to inhale their own exhaled air before reaching fresh air. This is what is referred to as "dead volume". For instance, when the inhalation chamber is installed in a mechanical-ventilation circuit after the Y shaped piece, the volume has to be minimal while being enough to optimize the inhalation of drug when the nebulizer or the MDI operates.

In other cases, when the nebulizer or the MDI do not operate and are not needed, the inhalation chamber should be dismantled from the circuit to avoid becoming dead volume, and adversely affect oxygenation of the patient. However, this operation would be difficult and non-trivial, as it requires that all the parameters of the respirator be modified.

There is described below an inhalation chamber with a tube 200 installed within the inhalation chamber to shunt the flow from the source of gas (and optionally, the aerosol from the MDI) that would have otherwise been introduced into the inhalation chamber, to the inside of the tube 200 only. The tube 200 is switchable under rotation from a closed position to an open position, where the tube is closed to the inhalation chamber or forms an opening into the inhalation chamber, respectively.

The tube 200 acts as an adjustable or reconfigurable duct which, when properly configured, can bypass or shunt the dead volume of the inhalation chamber 1 while crossing the inner volume of the inhalation chamber 1, or which can otherwise be configured to be opened to form a window with the inner volume of the inhalation chamber 1 that makes a fluid communication through this window between the lumen (i.e., longitudinal cavity) of the duct, now open, and the inner volume of the inhalation chamber. This open window can be located close to the point of connection of the nebulizer.

According to an embodiment, the duct is formed by two portions which each have a shape, the shapes being complementary such as to form the tube 200 when being properly mated together. For example, the shapes can be surface portions of a cylinder, thus being part-of-cylinder portions, both of which being complementary to form a cylinder when properly mated (e.g., two halves of a cylinder brought together, see FIGS. 8-10). This configuration ensures that mating the two portions will form a cylinder, hence the closed duct. The terms "duct" and "tube" are intended to refer to the same thing, although the term "duct" refers more specifically to the function of transporting a fluid regardless of the shape (which can be arbitrary), while the term "tube" refers more particularly to the tubular shape of the object.

Figure 8:
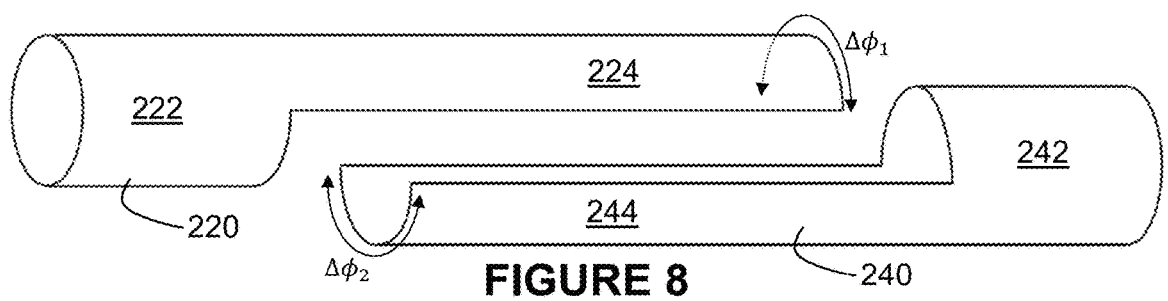
FIG. 8 is a side perspective view illustrating a first tube portion and a second tube portion, according to an embodiment.
Figure 9:
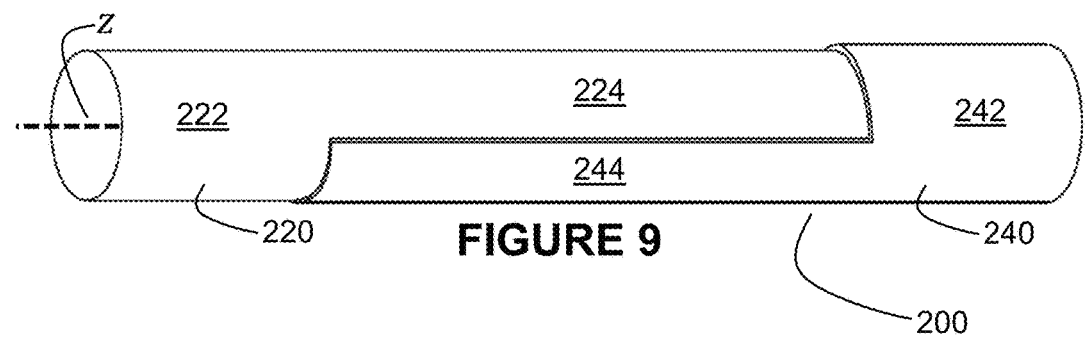
FIG. 9 is a side perspective view illustrating the first tube portion and the second tube portion forming the tube, according to an embodiment.
Figure 10:
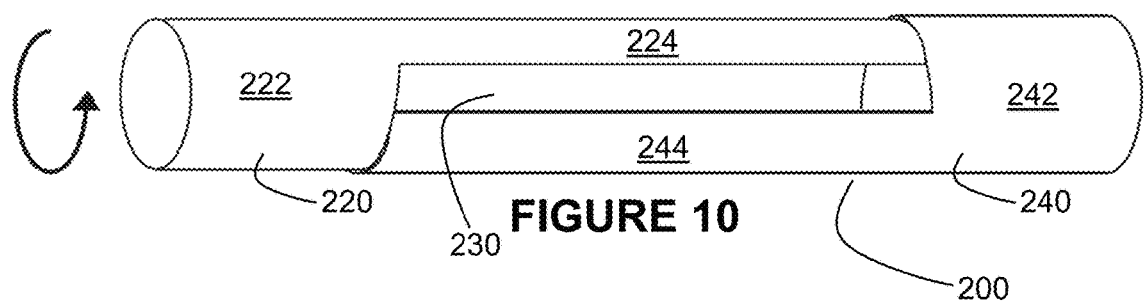
FIG. 10 is a side perspective view illustrating the first tube portion and the second tube portion being rotated in relation with each other to open or close the tube, according to an embodiment.

However, referring to FIGS. 8-10, these complementary portions (222, 242) should be displaceable by user action (e.g., relative rotation of the portions) to open the closed tube 200 to the inner volume of the inhalation chamber 1. Since the shapes are complementary to form a cylinder, when the complementary portions (222, 242) forming the cylinder are displaced away from their mating configuration, the displacement creates a window (or a plurality of windows) 230 on the surface of the tube 200. Such an action is performed when the nebulizer or the MDI is used, to allow the aerosol from the nebulizer or MDI, which is delivered to the inner volume of the inhalation chamber, to penetrate the lumen of the tube 200. In this case the complementary portions (222, 242) do not form a closed tube anymore since there is a window allowing penetration of the aerosol into the tube 200 from the inner volume of the inhalation chamber. According to embodiments, the tube being opened therefore may have a shape of a longitudinally cut tube, a "bevelled"-cut tube in which both portions (22, 242) have one of their ends diagonally transversely cut, or a tube with slots or openings, depending on the manner by which the portions of the tube 200 are allowed to be displaced in relation with each other.

Figure 1:
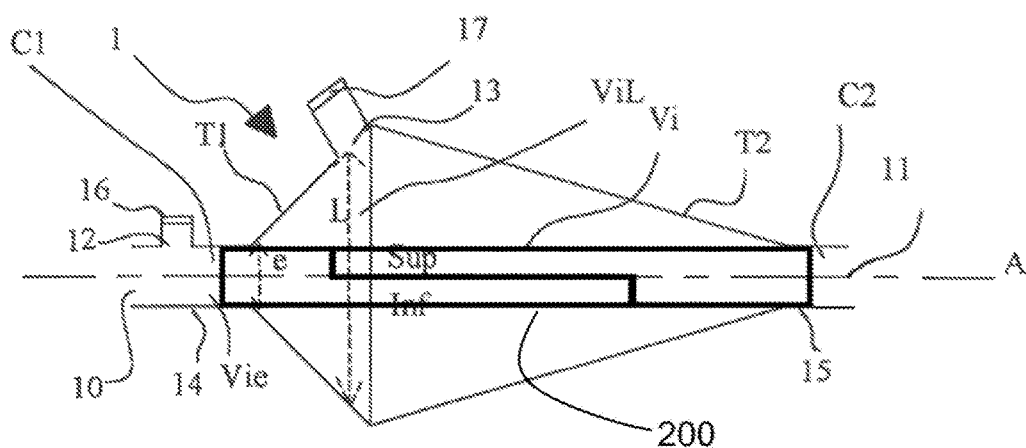
FIG. 1 is a cross section illustrating an inhalation chamber with a closed tube therein, according to an embodiment.

With reference to FIG. 1, there is shown an inhalation chamber 1 according to a first embodiment. The inhalation chamber 1 is, for example, made of polypropylene, and it defines an internal volume Vi for receiving particles from the nebulizer and/or the MDI, and to be crossed by a gas or aerosol stream generated by a mechanical-ventilation device.

The inhalation chamber 1 may comprise four openings. The first opening 10 (gas stream opening) is an entry for the gas stream emitted by a mechanical-ventilation device, such as air, and the second is an exit 11 for the same flow. According to the embodiment shown in FIGS. 1-7, these two openings are provided on the same longitudinal axis A of the inhalation chamber 1. The dimensions of the openings 10 and 11 are adapted to enable connection of the chamber 1 on the tubing of a conventional mechanical-ventilation device. Preferably, the duct or tube 200 connects the openings 10 (connection to a source of gas) and 11 (output to the patient) and extends directly (and uninterruptedly when forming a closed tube) between them. The third opening, or pMDI opening 12 may be used for receiving a MDI or pMDI, where the duct, or tube 200, should accommodate such an opening by comprising a corresponding opening (pMDI receptacle 229) which is secured within the third opening 12. The fourth opening may be a nebulizer opening 13 for receiving a nebulizer, such as a vibrating mesh nebulizer. The duct, which comprises portions that can move to open a window, should be displaced such that this window is formed close to the opening 13 for receiving a nebulizer in the inner volume of the inhalation chamber 1 to maximize the input of aerosol into the lumen accessible through the window.

According to an embodiment, the chamber longitudinal plane A separates the inhalation chambers in two portions. The openings 12 and 13 may be provided in a common portion of the inhalation chamber 1. When the chamber is incorporated into a mechanical-ventilation device, the common portion comprising the openings 12 and 13 is the upper portion (Sup) of the chamber, by opposition to the lower portion (Inf).

According to another embodiment, the inhalation chamber 1 may further comprise two frustoconical portions T1, T2, of which the large bases are common. It defines a large section L of the chamber 1 in a central region of the chamber 1 in which the internal volume is greater, as well as two narrow sections in which the internal volume is smaller close to the entry 10 and the exit 11, respectively. Cylindrical portions 14, 15 extend from the small bases of the inhalation chamber 1, the cylindrical portion 14 being in communication with the entry 10 for the gas stream, the cylindrical portion 15 being in communication with the exit 10 for the gas stream. In a specific embodiment, as will be discussed further below, one of the frustoconical portions, for example T2, can be formed by a conical surface extending outwardly from a base portion of the tube 200.

According to an embodiment, the slope of the frustoconical portion T1 leading to the entry 10 for the gas stream may be steeper and shorter than the frustoconical portion T2 leading to the exit 11 for the gas stream. The opening 13 for the nebulizer may be provided in the larger section L of the chamber 1 so that the emitted particles emerge where the internal volume is greater, noted ViL. The axis of the opening 13 may form an angle which is less than or equal to 90° with respect to the longitudinal axis A of the inhalation chamber.

According to an embodiment, the opening 12 for receiving the metered-dose inhaler may be provided, for its part, in a narrow section "e" of the chamber 1, preferably in the cylindrical portion C1 in communication with the entry 10 for the gas stream. In this case, the emitted particles thus emerge when the volume is smaller, denoted Vie. The volume Vie is smaller than the volume ViL. Furthermore, the opening 12 is located upstream of the opening 13 to avoid that particles emitted by the nebulizer obstruct by impaction the exit opening of the metered-dose inhaler when it is connected. Therefore, the opening 13 is located on the frustoconical portion T1 but could be placed on the frustoconical portion T2.

In embodiments, the openings 12 and 13 may comprise shutting means 16, 17, respectively, for sealably shutting them when no nebulizer and/or inhaler are connected to the inhalation chamber 1. Shutting means may include, for example, caps of suitable shape, membranes, shutters, sliders, or the like. The inhalation chamber 1 should be substantially sealed or airtight, to avoid requiring the tube 200 to be sealed as well.

Figure 2:
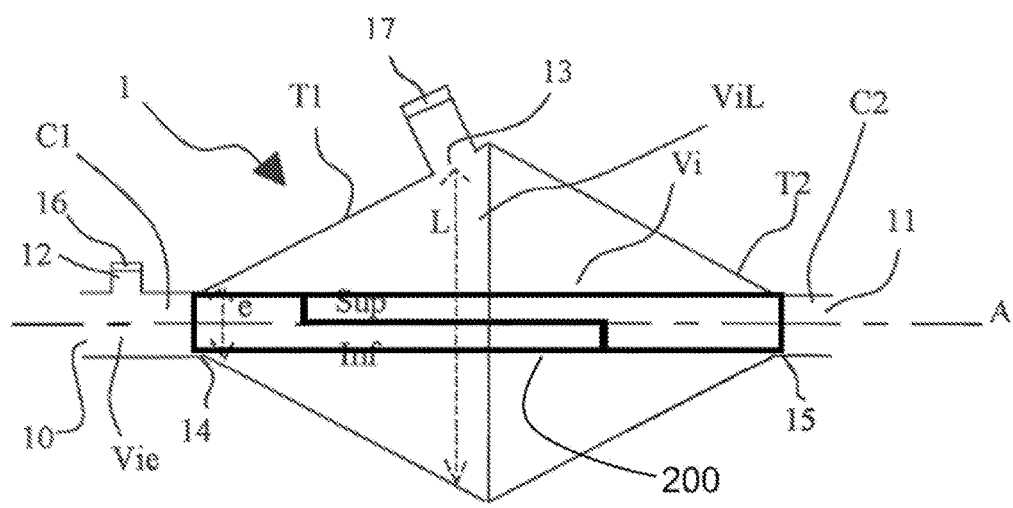
FIG. 2 is a cross section illustrating another embodiment of an inhalation chamber with a closed tube therein.

According to another embodiment, the inhalation chamber 1 shown in FIG. 2 comprises the same features as the inhalation chamber 1 represented in FIGS. 1 and 3 to 7, except the frustoconical portions T1, T2, are, according to this embodiment, symmetric, the slopes of the frustoconical portions T1, T2 may be identical.

Figure 3:
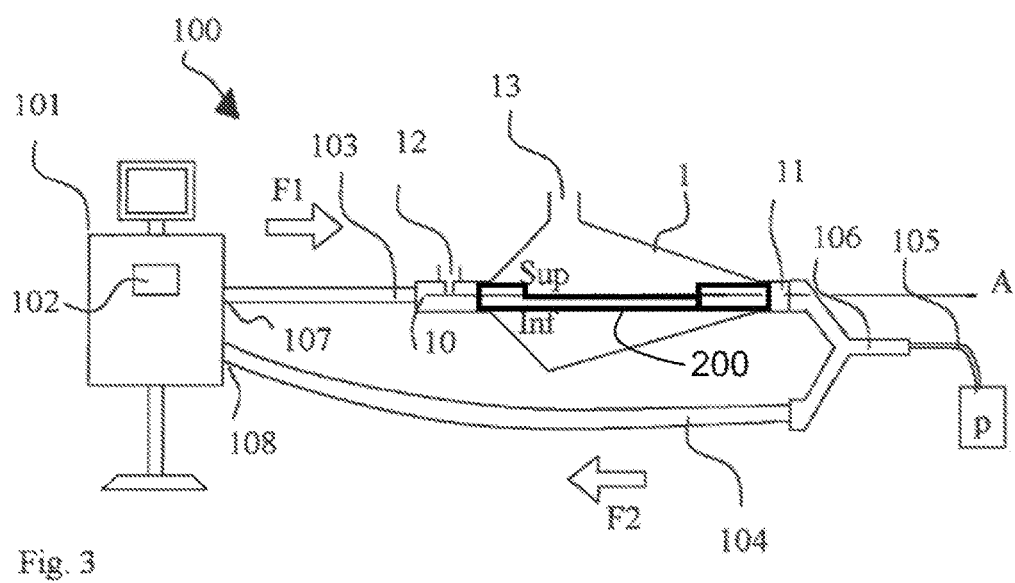
FIG. 3 is a cross section illustrating an inhalation chamber with an open tube therein, connected to a mechanical-ventilation device, according to an embodiment.

Now referring to FIG. 3, there is shown a mechanical-ventilation respiratory device 100 in which is incorporated an inhalation chamber 1 according to the present invention.

In embodiments, the device 100 typically comprises a respirator 101 to insufflate a gas volume to a patient. The respirator 101 may comprise a unit 102 capable of controlling gas stream and pressure, generally an air/oxygen mixture.

The device 100 comprises an inspiration or inhalation duct 103 intended to be taken by the gas stream during an inspiration or inhalation phase, and an expiration or exhalation duct 104 intended to be taken by the gas stream during an expiration (exhalation) phase, and a supply duct 105 for supplying the gas stream to the patient.

In embodiments, the inspiration duct 103 may be firstly connected to an exit 107 of the respirator 101, and secondly to an entry 10 of the inhalation chamber 1. The exit 11 of the chamber 1 may be connected to a Y-shaped piece 106, so that the inhalation chamber is located on the path taken by the gas stream during inspiration phases.

In embodiments, another branch of the Y-shaped piece 106 is linked to the duct 105 connected to the patient. Furthermore, in some embodiments, the duct 105 can be replaced by a mask worn by the patient, depending on the situation.

The expiration duct 104 may be connected, firstly, to the third branch of the Y-shaped piece 106, and secondly, to an entry 108 of the respirator 101.

The inhalation chamber 1 may be linked to the device 100 so that the openings 12 and 13 for connecting, respectively, the nebulizer and the MDI, are on the top of the chamber 1, i.e. in the upper portion (Sup) separated from the lower portion (Inf) by the longitudinal plane A of the chamber 1.

The device 100 thus defines a circuit for the gas stream. Arrows F1 and F2 represent the circulation of the gas stream during an inspiration phase and an expiration phase, respectively.

Figure 4:
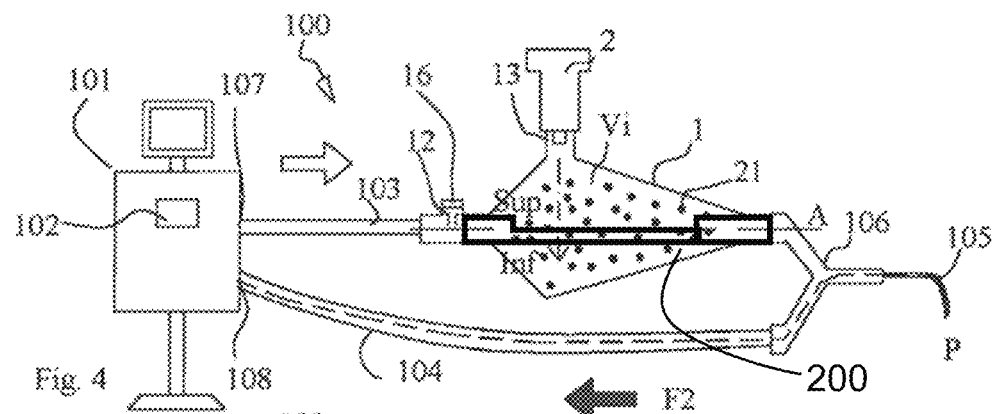
FIG. 4 is a cross section illustrating an inhalation chamber with an open tube therein, with a nebulizer in operation, connected to a mechanical-ventilation device, according to an embodiment.
Figure 5:
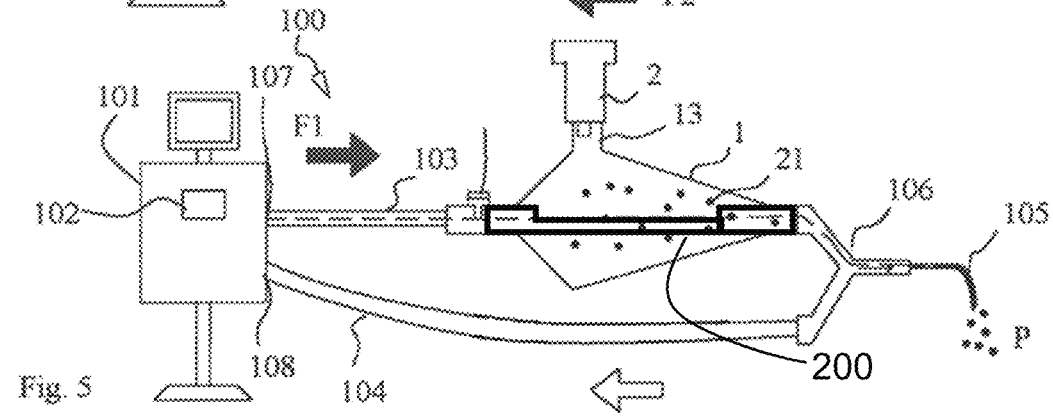
FIG. 5 is a cross section illustrating the inhalation chamber of FIG. 5 after the nebulizer is operated.

In reference to FIGS. 4 and 5, there is described an inhalation chamber 1 included in a mechanical-ventilation device 100 when a nebulizer 2, such as a vibrating mesh nebulizer, is used and thus connected to the inhalation chamber 1 in its upper portion (Sup).

FIG. 4 represents an air expiration phase by the patient. The gas stream expired by the patient crosses the duct 105, follows the Y-shaped piece 106 and then the expiration duct 104 (arrow F2). The aerosol produced by the nebulizer 2 is stocked in the inhalation chamber 1 and is introduced into the tube 200 which is in an open position, with the opening defined toward the upper portion (Sup). To do so, the nebulizer 2 is operated and the nebulized particles enter the internal volume Vi of the chamber 1 along a vertical projection axis. The particles being projected in the larger section of the chamber, the volume ViL is sufficient to limit their deposition by impaction against the walls of the chamber, or their sedimentation.

During the next inspiration phase (referring to FIG. 5), the gas stream (arrow F1) follows the inspiration duct 103 from the respirator 101 and crosses the inhalation chamber 1 and the open tube 200, dragging along the nebulized particles 21 projected into the opening of the tube 200 towards the patient using the Y-shaped piece Y 106 and tube 105.

The opening 12 for receiving the inhaler is closed by shutting means 16, for examples caps or suitable shape, membranes, shutters, sliders, or the likes, and is therefore sealable.

Figure 6:
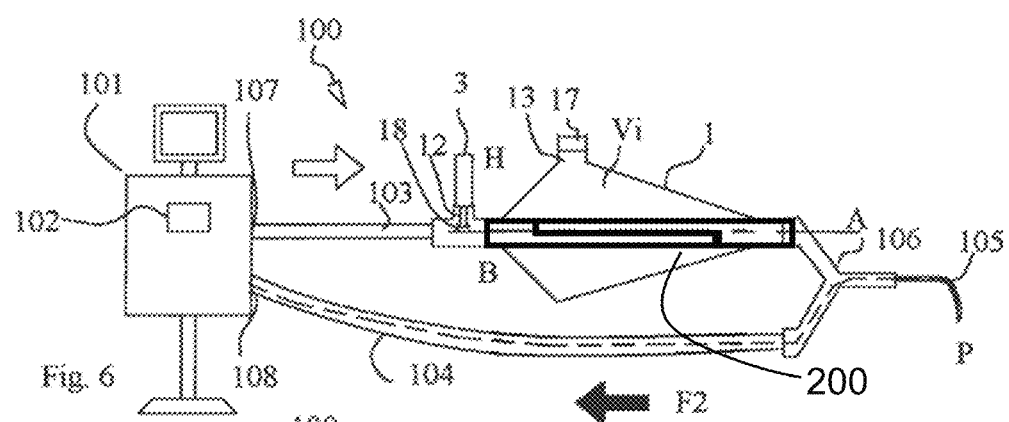
FIG. 6 is a cross section illustrating an inhalation chamber with a closed tube therein, with a pMDI in operation, connected to a mechanical-ventilation device, according to an embodiment.
Figure 7:
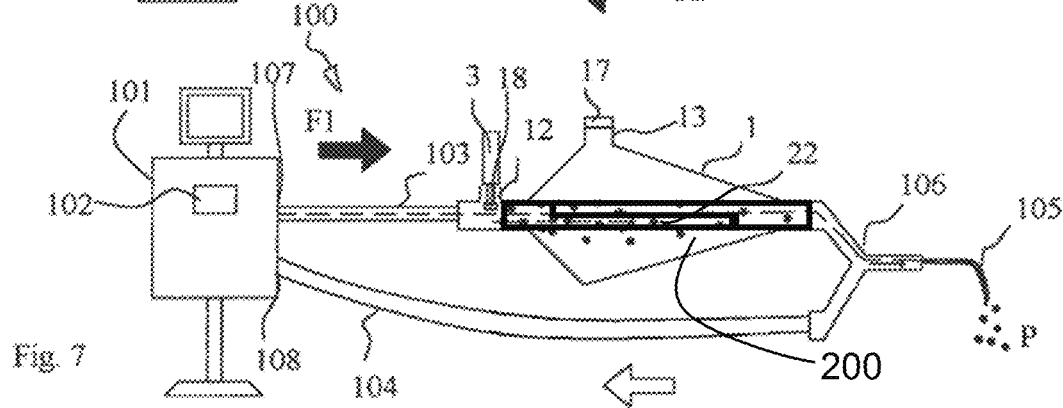
FIG. 7 is a cross section illustrating the inhalation chamber of FIG. 6 after the pMDI is operated.

Now referring to FIGS. 6 and 7, there is described an inhalation chamber 1 working in a mechanical-ventilation device 100 when an inhaler 3 is used and thus connected to the inhalation chamber 1 on the opening 12, with the tube 200 in closed position to bring the aerosol from the pMDI to the patient with the lowest dead volume.

FIG. 6 represents an air expiration phase by the patient. During this expiration phase, everything works as explained with reference to FIG. 4, with the difference that no particle produced by the metered-dose inhaler 3 is stocked in the inhalation chamber 1.

At the beginning of the next inspiration phase, the inhaler 3 is manually started by a practitioner or coordinated by other means (e.g. electronic or sensor means) with the beginning of the inspiration phase. After starting of the inhaler, particles enter the internal volume Vi of the chamber 1 along a horizontal projection axis. Indeed, the opening 12 comprises means for directing the aerosol flow along an axis horizontal with respect to the axis A of the inhalation chamber 18, such as a spraying nozzle, and then into the tube 200.

The particles are projected along a horizontal axis, and thus parallel to the longitudinal axis A of the chamber 1, in a narrow section "e" of the chamber 1 and close to the entry 10 for the gas stream. The volume Vi is sufficient to limit their deposition by impaction against the walls of the chamber, or their sedimentation. The particles projected along a horizontal axis, and thus parallel to the longitudinal axis A, are also projected into the tube 200, along the longitudinal axis of the tube 200, as shown in FIGS. 6-7. If the tube 200 is in closed position, the particles remain confined within the tube 200.

The gas stream that is generated by the respirator 101 takes the inspiration duct 103 and then crosses the inhalation chamber 1, dragging along particles 22 towards the patient using the Y-shaped piece 106 and tube 105.

It is of course possible to simultaneously use a metered-dose inhaler and a nebulizer during the same respiratory cycle, in which case the tube 200 needs to be in open position, defining an opening toward the opening 13 for receiving the nebulized particles or droplets. Since the nebulizer is located downstream of the metered-dose inhaler, the particles produced by the nebulizer cannot impact themselves on the inhaler and its emitted particles.

Furthermore, the inhalation chamber as described with reference to FIG. 2 in a mechanical-ventilation respiratory device works identically as described with reference to FIGS. 4 to 7.

Referring to FIGS. 8-10, there is shown a tube 200 to be provided within and across an inhalation chamber 1, or spacer, for shunting the inhalation chamber 1. In other words, the inhalation chamber 1 can be by-passed by a reconfigurable tube extending through it.

According to another embodiment, and as shown in FIGS. 1-3, the tube 200 may comprise a first tube portion 220 and a second tube portion 240, where the second tube portion 240 mates with the first tube portion 220 to allow one of them to rotate along the longitudinal axis (i.e., spin) while having its outer surface slide with the inner surface of the other (slightly larger) one. The first tube portion 220 and the second tube portion 240 can rotate in relation to each other (i.e., the movement is relative since one of the portions can be fixed).

The tube 200 is to be installed inside an inhalation chamber, such as the inhalation chamber 1. The tube 200 should have a variable configuration (i.e., its shape is reconfigurable) to define an open position in which the tube 200 has openings (e.g., a half-cylinder or other part-of-cylinder portion being open, or alternatively, longitudinally-extending slots or windows which are periodic over the azimuth), and a closed position in which the tube 200 is a closed duct. The configuration is variable in that the tube 200 can be acted upon, as described in greater details below, to switch from the closed position to the open position, or from the open position to the closed position, as well as intermediate closed/opened positions which may be attained.

Figure 13:
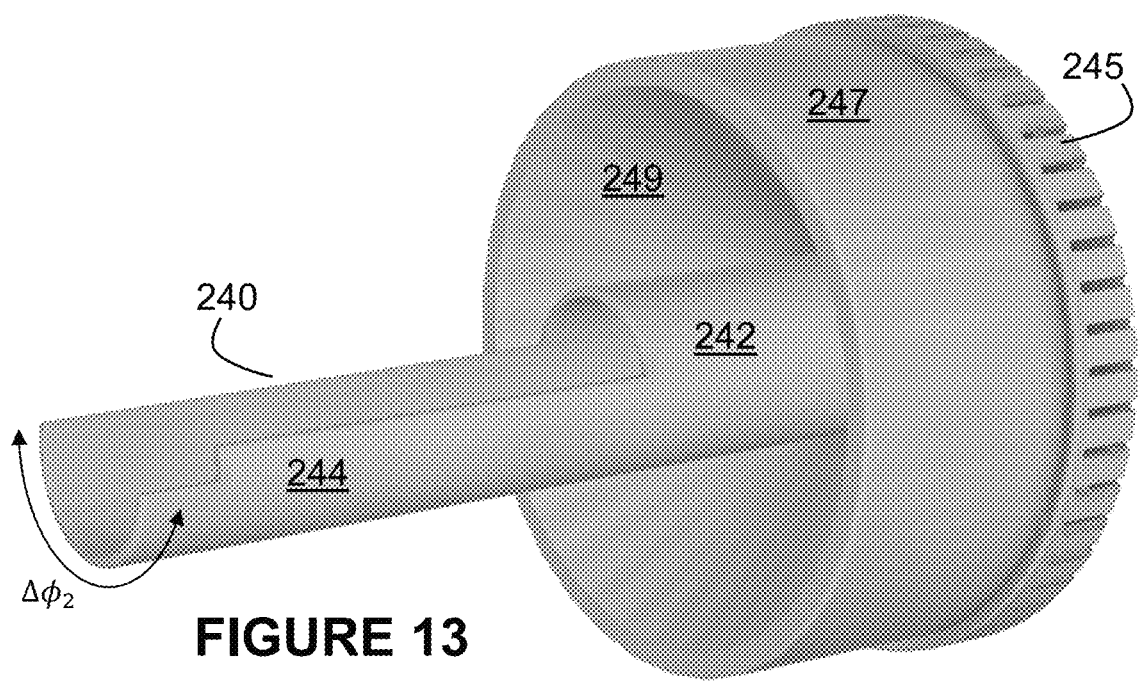
FIGS. 13-14 are side perspective views illustrating the second tube portion, according to an embodiment.
Figure 14:
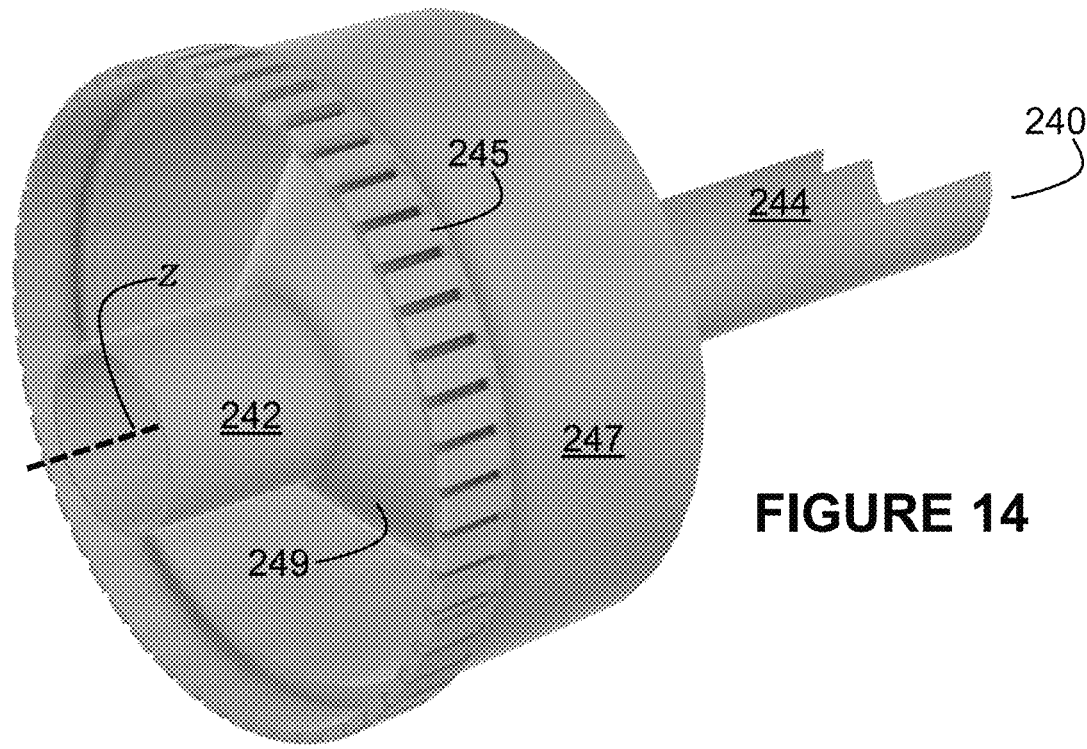

To perform this switch between open and closed positions, the first tube portion 220 and the second tube portion 240 are allowed to rotate in relation to each other. Therefore, at least one of the first tube portion 220 and the second tube portion 240 is rotatable with respect to the other one. According to an embodiment, the second tube portion 240 is rotatable using a mechanical part reaching the outside of the inhalation chamber 1 and upon which the user can act. For example, the second tube portion 240 may be connected to an annular portion 245, or ring, that is accessible to the user, who can turn the annular portion 245 to directly cause the second tube portion 240 to rotate within the inhalation chamber 1. Since only one tube portion is in rotation, there is a relative variation in the azimuthal angle between both tube portions 220, 240 which eventually results in switching from the open position to the closed position and from the closed position to the open position, and of course any intermediary position therebetween. The annular portion 245 is shown in FIGS. 13-14, and can advantageously be sandwiched between two portions of the inhalation chamber 1, these two portions being shown in FIGS. 15-16, to be accessible to the user and rotated. The annular portion 245 is thus sandwiched in a slot formed on the surface of the inhalation chamber 1, the slot extending around the whole contour of the surface of the inhalation chamber 1.

Figure 15:
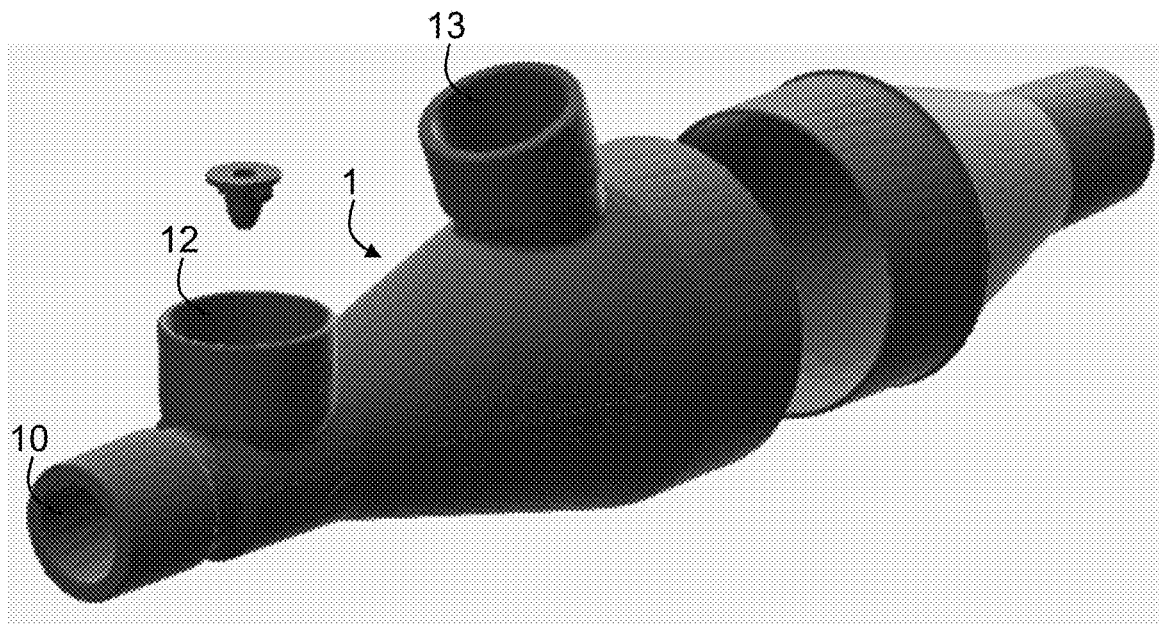
FIGS. 15-16 are side perspective views illustrating the inhalation chamber, according to an embodiment.
Figure 16:
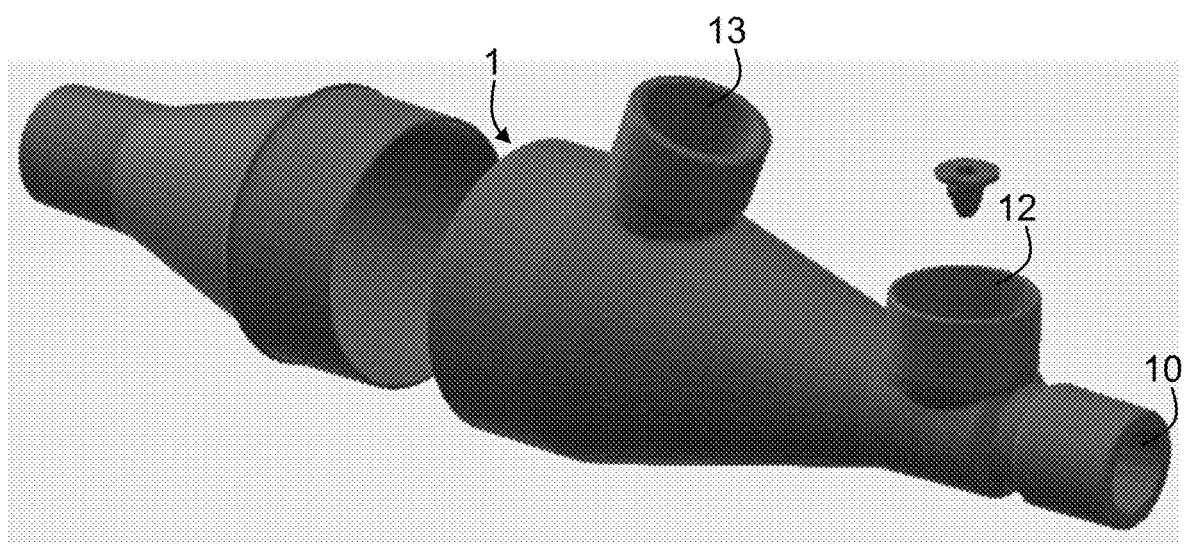
Figure 17:
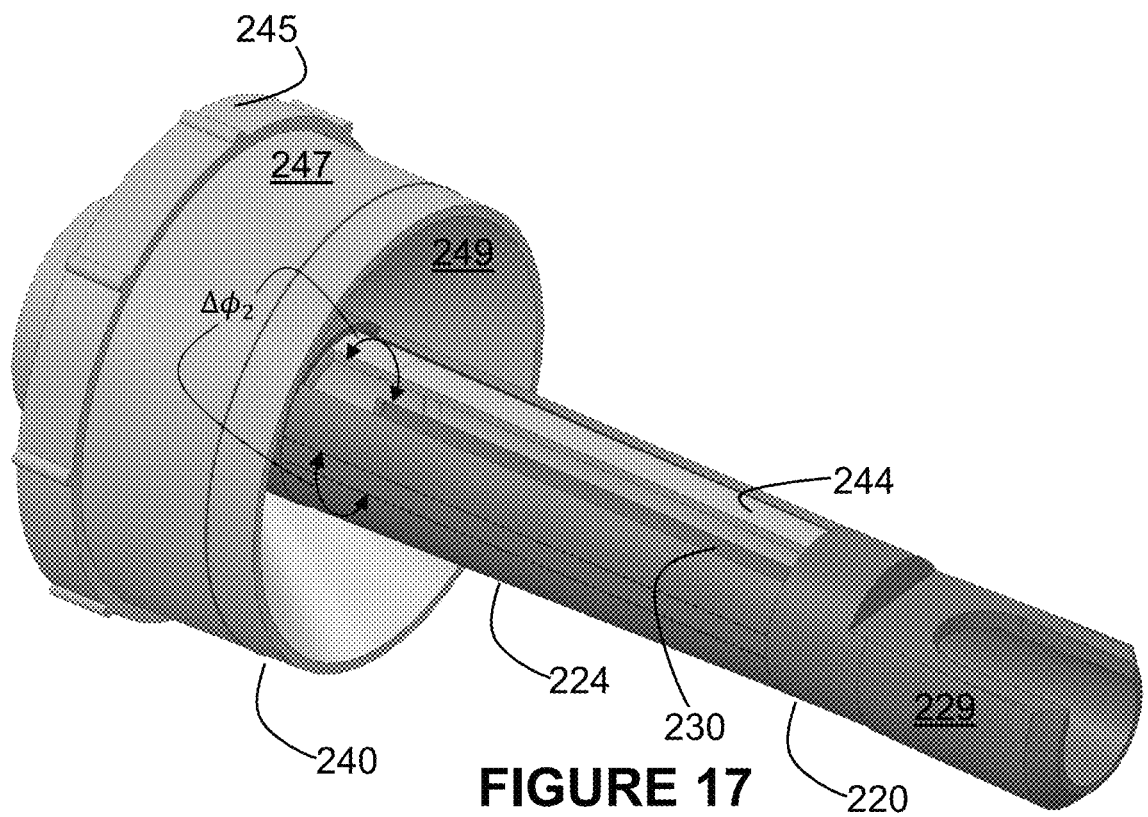
FIGS. 17-19 are side perspective views illustrating the first tube portion and the second tube portion being rotated in relation with each other to open or close the tube, according to an embodiment.
Figure 18:
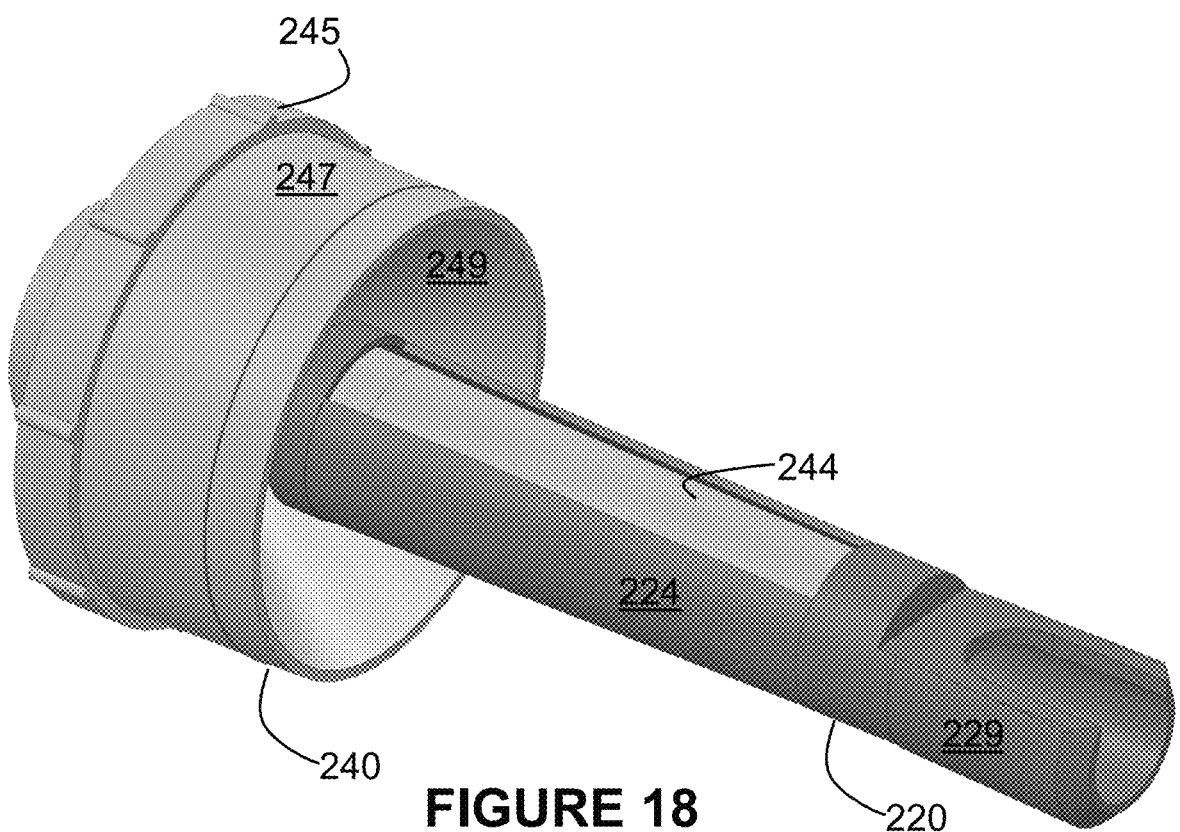
Figure 19:
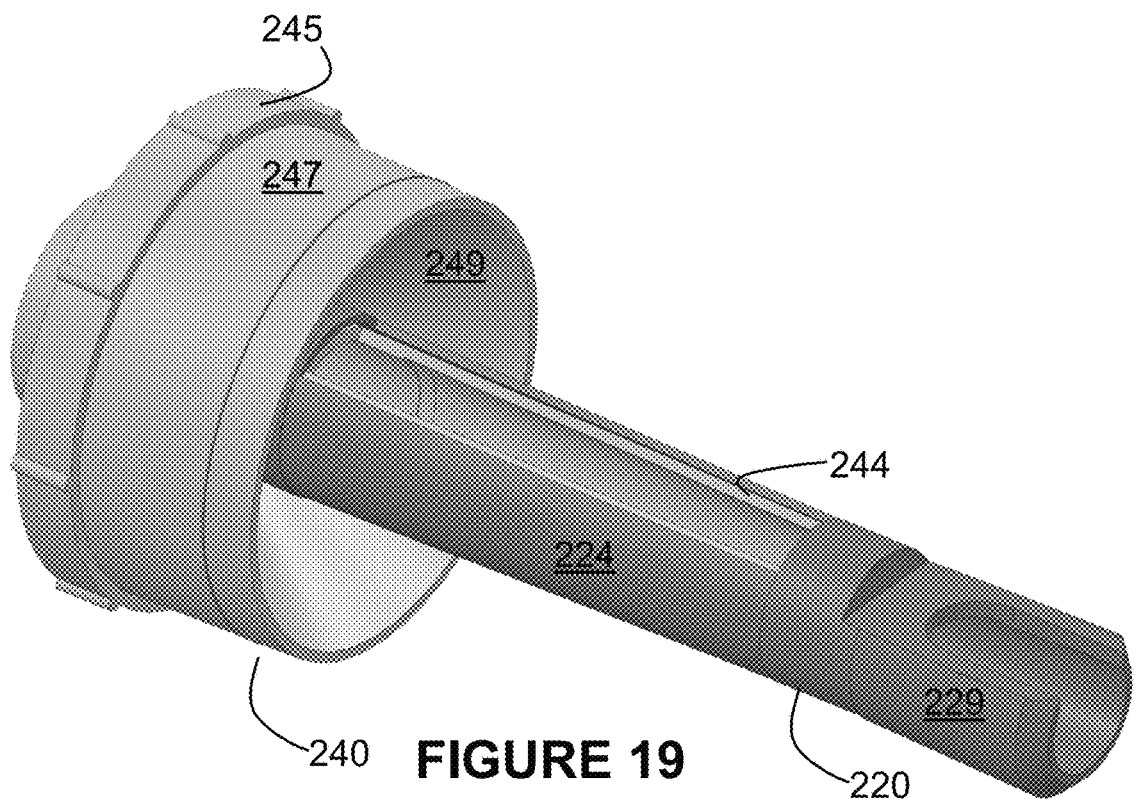

This annular portion 245 can be at a contour of a cone surface 249, as shown in FIGS. 17-19. More specifically, according to another embodiment which comprises a cone surface 249 starting from a base portion 242 and which forms a wall of the inhalation chamber (e.g., the frustoconical portion T2). This cone surface 249 extends outwardly toward a center of the inhalation chamber 1 from the base portion 242. It ends at a mating surface 247 which is shown as being cylindrical and which mates with another portion of the inhalation chamber 1 in a way similar to the two-portion inhalation chamber of FIGS. 15-16. In this case, the second tube portion 240 can be the second portion of the inhalation chamber which mates with a first portion of the inhalation chamber as shown in FIGS. 15-16 and where such a first portion comprises the input connectors or openings (12, 13) for the pMDI and the nebulizer. The mating surface 247 can comprise the annular portion 245 at an edge thereof, which implies that the annular portion 245 is not sandwiched but rather provided at an edge of the inhalation chamber where it can be rotated.

According to another embodiment, the annular portion 245 may be replaced by a non-annular protrusion which extends from the second tube portion 240 to a surface of the inhalation where a slot is provided. The user can move the protrusion extending outwardly to the slot and thus perform the rotation. This protrusion can also reach an edge of the inhalation chamber instead of a slot and be rotated from this edge.

According to another embodiment, the first tube portion 220 may be fixed to the inhalation chamber. A pMDI receptacle 229 may be provided and be secured below the pMDI opening 12. The pMDI receptacle 229 is a cylindrical portion continuous with the base portion 222 and having an opening by which the tip of the pMDI protrudes into the lumen of the first base 220, thus reaching the closeable lumen of the duct or tube 200 by the opening 10 where the duct or tube 200 starts.

In embodiments, to be able to rotate, the first tube portion 220 and the second tube portion 240 should be mating with each other, with slightly different diameters of conforming cylinder portions from both the first tube portion 220 and the second tube portion 240, to allow sliding in a rotation movement. At least one of the first tube portion 220 and the second tube portion 240 should be moveable by the user, the configuration allowing the user to grip one of the first tube portion 220 and the second tube portion 240.

Figure 20:
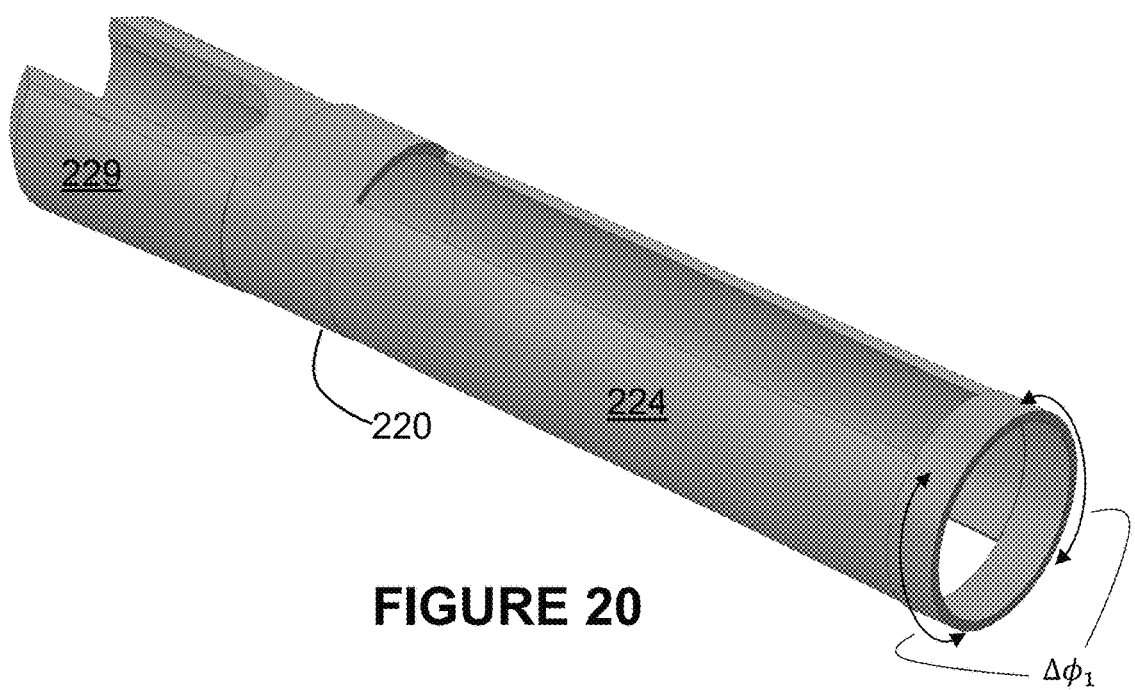
FIG. 20 is a side perspective view illustrating the second tube portion, according to an embodiment.

Alternatively, the user can indirectly act on a tube portion using a mechanism to transmit movement (the annular portion 245 as mentioned above, or from a handle, a wheel, or a dimmer) or an electronic circuit that acts on the tube portion, using a mechanism actuated by the electronic circuit, to provide the appropriate rotation movement in the azimuthal direction. Alternatively, the mechanism to transmit movement can comprise any protrusion (ring or other shape such as a rod or pin) extending from one of the portions, such as the second portion 240, outwardly toward a surface of the inhalation chamber where a slot is provided to act on the protrusion to induce the rotation. This protrusion can also be made to reach an edge of the inhalation chamber which does not appear as a slot, such as shown for the annular portion 245 of FIGS. 19-21, i.e., at an edge of a mating surface 247 of the second portion 240 in which the second portion 240 also forms a wall of the inhalation chamber 1 with the cone surface 249.

According to an embodiment, the first tube portion 220 and the second tube portion 240 are shaped to mate and, when mated, have a shape of a cylinder, thereby making a tube together as a whole. The first tube portion 220 and the second tube portion 240 should thus be at least a complement to each other to form a cylinder. The terms "at least" imply that some overlap between parts of the first tube portion 220 and the second tube portion 240 should be expected. For example, two halves of cylinder are complementary shapes. Another example would be a tube with a window cut therefore, and another portion comprising a cover with the shape that would at least fill the window. Furthermore, the outer diameter of one of the semi-cylindrical portions may be slightly smaller than the inner diameter of the other semi-cylindrical portion to allow one of them to slide with respect to each other when being rotated and keep the overlap of portions substantially tight, although complete tightness is not required since the inhalation chamber 1 is sealed with respect to the outside (i.e., the ambient environment where the inhalation chamber 1 is used. Therefore, the slidable mating does not imply airtightness, which makes the manufacturing simpler.

Figure 11:
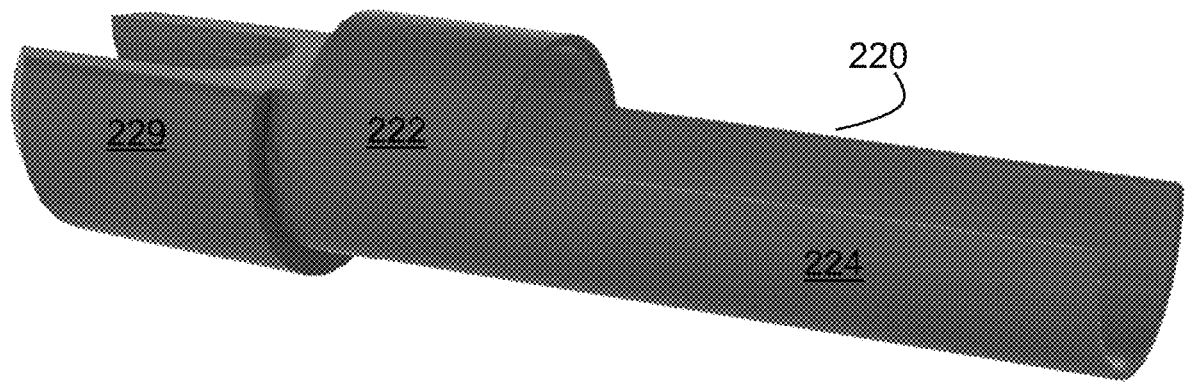
FIGS. 11-12 are side perspective views illustrating the first tube portion, according to an embodiment.
Figure 12:
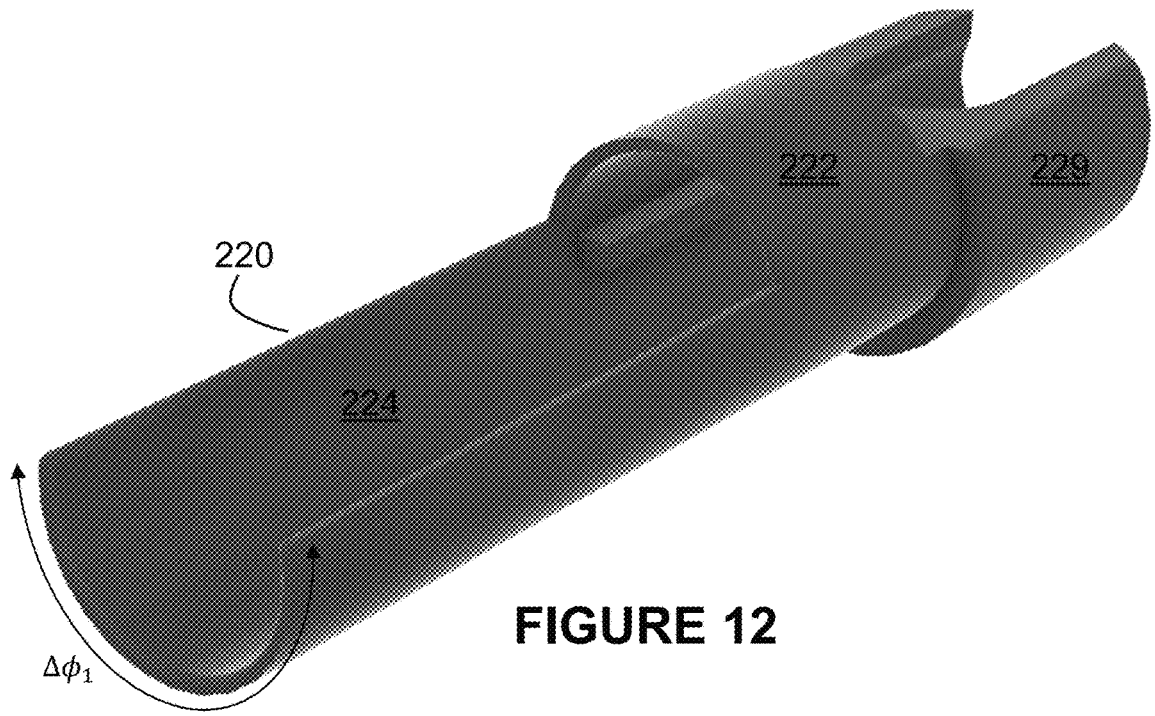

Exemplary embodiments of the first tube portion 220 and the second tube portion 240 are shown in FIGS. 8-14 and 17-20. The first tube portion 220 comprises a cylinder base 222, which is a hollow cylinder installed by the first opening 10 of the inhalation chamber 1 (which receives the third opening 12 from the pMDI), preferably installed within the cylindrical portion 14, or directly downstream (i.e., distal to) the cylindrical portion 14. The cylinder base 222 may also be integrally connected to the cylindrical portion 14 of the inhalation chamber, as shown in FIGS. 11-12. The cylinder base 222 may be a complete cylinder in that the solid portion covers the whole azimuth $\phi$, from 0° to 360°, for substantial complete coverage along the longitudinal axis z, where the azimuth $\phi$ and longitudinal axis along z are defined in the conventional way (same definition as in the ISO 31-11 standard, incorporated herein by reference).

The first tube portion 220 further comprises a semi-cylindrical cover 224 (namely the first semi-cylindrical cover 224) that extends distally from the cylinder base 222. It extends in the z direction, where the longitudinal axis z is the longitudinal axis of the half cylinder defined by the semi-cylindrical cover 224.

The first and the second semi-cylindrical covers 224, 244 should at least completely overlap along the longitudinal axis z to ensure that the first semi-cylindrical cover 224 reaches and mates with the second cylinder base 242 and the second semi-cylindrical cover 244 reaches and mates with the first cylinder base 222, as shown in FIGS. 9-10. The second cylinder base 242 may be housed in the cylindrical portion 15, in which it can rotate, to have the tube communicate with the exit 11.

As used herein, the term semi-cylindrical refers to the fact that the semi-cylindrical cover has a curved shape, preferably of a circular nature. The arc of circle thus created extends in the z-direction to form a section of cylinder. Since the arc of circle is approximately a half-circle, the cover 224 is considered substantially "semi-cylindrical" or "hemi-cylindrical", although the arc of circle defining the first semi-cylindrical cover 224 may extend in the azimuthal direction for more or less than 180°, for example between 170° to 190°, or 150° to 210°, or 120° to 240°, or 170°, 180°, 190°, 200°, 210°, 220°, 230°, 240°. The value of the extension of the semi-cylindrical cover for a given azimuth is herein defined as the azimuthal range. In embodiments, the azimuthal range of the first semi-cylindrical cover 224 ($\Delta\phi_1$) and of the second semi-cylindrical cover 244 ($\Delta\phi_2$) should add up to at least 360° ($\Delta\phi_1+\Delta\phi_2\geq360°$). This condition is to ensure that there is at least one value of the relative azimuth $\phi_{1,2}=\Delta\phi_1+\Delta\phi_2$ between the first tube portion 220 and the second tube portion 240 for which the whole azimuthal range of the combined semi-cylindrical covers 224, 244 is actually covered by at least one of them. As described further below, the azimuthal range of coverage can be split into more than one sub-portion, such as to provide a plurality of windows which can be periodic over the azimuthal range, where the plurality of covers adds up to the azimuthal coverage of $\Delta\phi_1$ or $\Delta\phi_2$.

By rotating the second semi-cylindrical cover 244 with respect to the first semi-cylindrical cover 224 into the open position, the semi-cylindrical covers overlap, preferably in the lower portion (Inf) of the inhalation chamber 1. The first and second tube portions 220, 240 thus define an opening of the tube 200 toward the upper portion (Sup). The opening is thus advantageously directed toward the opening 13 for the nebulizer, such that when the tube 200 is in open position, the particles from the nebulizer are effectively projected into and/or toward the tube 200.

Advantageously, providing the tube within the inhalation chamber takes away the requirement of a sealed tube. Indeed, if the tube was located outside any other component, the tube would need to be sealed to avoid the aerosol from escaping the tube or to maintain the proper pressure inside the tube when the tube is in a closed position. Having a sealed tube in closed position requires very accurate diameters for both cylinder portions and the use of sealing member to maintain the seal at the junction of both tube portions 220, 240.

The use of the tube 200 is advantageous in that it allows the user from the nursing staff to use the inhalation chamber 1, connected as it is, regardless of the whether the nebulizer is needed or not. Therefore, in order to switch from a use where the nebulizer is needed to a use in which it is not needed, there is no need to disconnect the inhalation chamber 1, thanks to the presence of the tube 200 to shunt the inhalation chamber 1, reduce the dead volume and avoid using the nebulizer that would be unnecessary.

The tube 200 is usable on different sizes of the inhalation chamber 1 described. It is also workable with other types and shapes of inhalation chambers. The tube 200 is advantageous for inhalation chambers where the pMDI and the nebulizer are located on different openings on the inhalation chamber, and where the pMDI feeds the proximal end of the tube 200 (i.e., the first cylinder base 220).

The tube 200 may be used for shunting the inhalation chamber 1 rather than changing the volume of the inhalation chamber 1. The tube 200 thus enables removal of the dead volume from the inhalation chamber 1 without having to give the inhalation chamber a variable volume, for example by providing walls with an accordion shape of with bellows. The accordion walls give greater complexity to the inhalation chamber, and may fail to reduce dead volume because of the interstices inherent to the accordion shape, or may cause undesirable aerosol deposition on the walls.

Now referring to FIGS. 17-20, there is shown another embodiment in which each of the tube portions or covers 224, 244 forming the tube are not semi-cylindrical, but are still part-of-cylinder portions. The tube portions 224, 244 are shown as being two portions of a quarter-cylinder. The overall azimuthal range covered, $\Delta\phi_1$ and $\Delta\phi_2$, are thus the same as with the half-cylinder, but instead of a single window formed when the tube 200 is opened, there are two windows instead, which are proportionally (e.g. twice) smaller.

Although the duct is discussed above as being cylindrical and thus forming a tube, the duct can have a varying diameter as long as the two-part duct has a shape which is the result of a revolution (i.e., a revolution surface) since the two parts are rotatable. Examples of revolution surface include a cylinder, a cone, or any deformed cylinder with a diameter that varies along its length while remaining symmetrical with respect to its longitudinal axis (which is the axis about which the revolution surface is defined).

Other shapes or configurations of covers can be implemented as long as they offer the same possibility of modifying the opening between the covers of the tube portions forming the tube together. For example, although the relative displacement between the first tube portion and the second tube portion is described as a rotation, a translation would also be possible as long as one of the portions defines a window, normally obstructed by the other portion, and where this other portion can be pulled or pushed along the longitudinal axis to uncover the window.

If the portions forming the duct are not to be rotated, then the duct can be provided in other shapes which do not need to be cylindrical or otherwise defined as a revolution surface. Instead, the duct can extend with a cross-section that would be a square, a rectangle, a polygon or an irregular shape, although still preferably rigid.

In addition to the tube 200, one may perform a method for operating an inhalation chamber. A duct or tube 200 as described above is installed in the inhalation chamber and extends from a metered-dose inhaler input to a patient output, the duct comprising two portions, each having a shape, the shapes being complementary to form the duct, and displaceable in relation with each other. One of a MDI (or pMDI) and a nebulizer is connected to the inhalation chamber. If the MDI is connected, a relative displacement is made between the two portions of the duct to close the duct and shunt the dead volume of the inhalation chamber, making a direct passage from the pMDI to the patient. If the nebulizer is connected, a relative displacement is made between the two portions of the duct to open the duct and form a window open to an inner volume of the inhalation chamber where the nebulizer is dispensing aerosol.

Although the apparatus was described above referring to a metered-dose inhaler and to a nebulizer, the tube 200 could be applicable, more generically, to an inhalation chamber comprising at least one opening for dispensing aerosol, where the tube 200 is used in the position which best transports the aerosol dispensed therefrom. In order to benefit from the different modes of aerosol transport offered by the adjustable tube 200, the inhalation chamber should provide at least two openings for dispensing aerosol. At least one of the aerosol dispensers (such as a MDI/pMDI) to be connected at these openings, formally the first aerosol dispenser, would be connectable at one end of the tube (preferably the one opposite the patient end). In this particular case, at least another one (such as a nebulizer), formally the second aerosol dispenser, would be connectable on a surface of the inhalation chamber, away from the ends of the tube 200 and facing an eventual window 230 formed on the tube 200. In replacement or in addition to the aerosol dispensers mentioned above, other openings can be provided on the surface of the inhalation chamber and can face a dedicated window to be formed on the tube 200, thus enabling simultaneous or selective dispensing of aerosol in the inhalation chamber.

According to an embodiment, the tube 200 can be opened or closed in order to modulate or have an effect on the aerosol transport from one aerosol dispenser. For example, in a case where there is only one aerosol dispenser connected to the inhalation chamber, such as a MDI/pMDI, the tube 200 can be opened or closed or have an intermediate position, thus acting on the rate or magnitude of aerosol transfer between the lumen of the tube 200 and the inner volume of the inhalation chamber 1. This action can change the dead volume (for aerosol transported from one end to the other end of the tube 200), or can change the rate of aerosol transported from the inner volume of the inhalation chamber 1 to the lumen of the tube 200 (for aerosol dispensed to the inner volume of the inhalation chamber). Therefore, there can be advantages of using the tube 200 in various positions regardless of the number or position of the aerosol dispenser(s).

It will be noted that the tube 200 may be used for the adjustment of effective volume in the context of ventilation, without necessarily having to transport a jet of aerosol therethrough.

Figure 21:
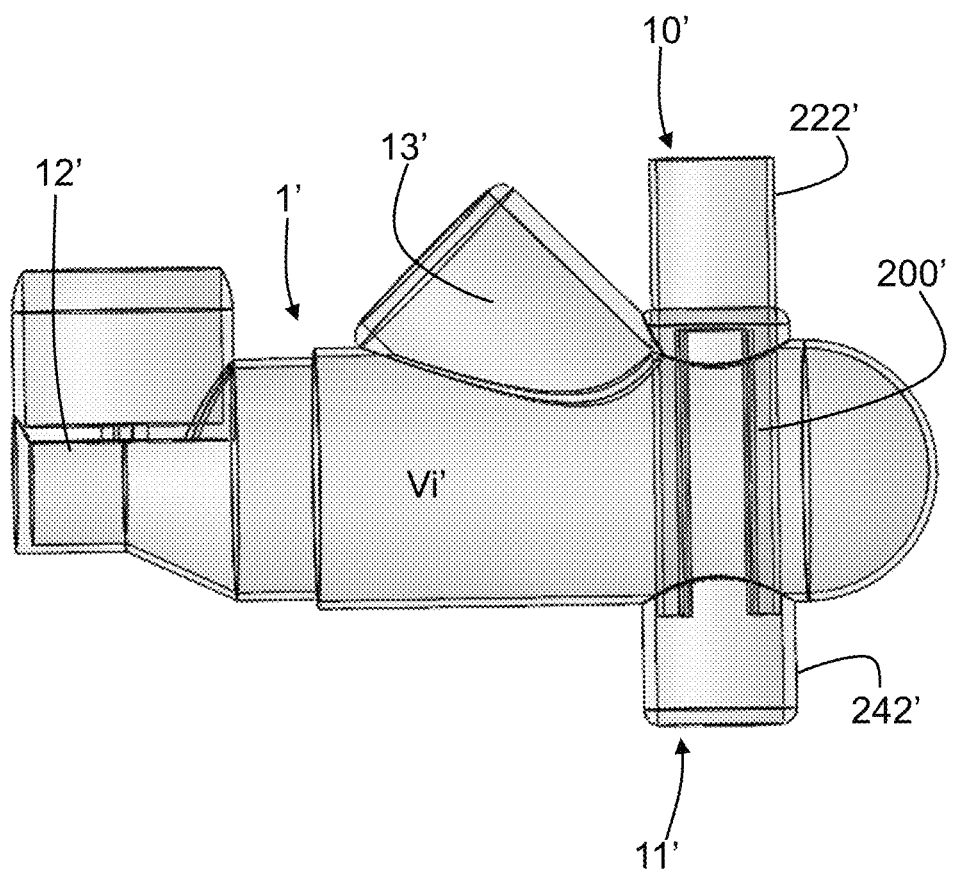
FIG. 21 is a side view illustrating another embodiment of an inhalation chamber with a tube therein.

For example, as shown in FIG. 21, the tube 200' may traverse the inhalation chamber, or spacer, without reaching the pMDI opening 12' on the inhalation chamber 1'.

In FIG. 21, the inhalation chamber 1' differs from the inhalation chamber 1 of FIGS. 1-7 in that the opening 10' to the source of gas is uncoupled from the pMDI opening 12, as it is displaced elsewhere on the inhalation chamber 1', closer to the patient output opening 11'.

Accordingly, the tube 200' may traverse the inhalation chamber 1', or spacer, through the short (transverse) axis of the inhalation chamber, instead of the longitudinal axis. This is particularly advantageous in a context of ventilation when a patient receives a gas for which communication with the pMDI or nebulizer is not necessary.

As described above in relation with FIGS. 1-7, the tube 200' may be closed such as it does not open toward the inside of the inhalation chamber. However, by having the tube 200' traverse the inhalation chamber along a short axis (FIG. 21), the dead volume of the tube 200' is minimized, especially when compared to the other situation (FIGS. 1-7) in which the tube 200 would traverse the inhalation chamber along its longest (longitudinal) axis.

In other words, the longitudinal axis of the tube 200' can be parallel or even coincident with the longitudinal axis of the inhalation chamber, as shown in FIGS. 1-7, or may instead be in another angle. As an example of another angle, the longitudinal axis of the tube 200' may be perpendicular to the longitudinal axis of the inhalation chamber 1', as shown in FIG. 21, in which the tube 200' is said to traverse the longitudinal axis in a transverse axis, i.e., across a shorter section (or the shortest section) of the inhalation chamber 1'.

Having the tube 200' traverse the longitudinal axis in a transverse axis, i.e., across a shorter section of the inhalation chamber, is useful to ensure that the tube 200' is short, thus minimizing its volume. Minimizing its volume helps minimizing the dead volume in the case were the tube 200' is closed and serves only as a passage for gas not coming from the inhalation chamber 1' and coming only from the source of gas from the opening 10'. In this case, the tube 200 does not extend from the aerosol opening 12'. The tube 200 rather selectively opens or closes toward the inner volume Vi' of the inhalation chamber 1', and the aerosol is dispensed into this inner volume Vi', to be transported into the tube 200' depending on whether the tube 200' is open or closed. The open state allows fluid exchange between the tube 200' and the inner volume of the inhalation chamber (comprising the aerosol). The closed state creates a bypass by which the tube 200' prevents the exchange of fluid with the inhalation chamber and rather forms a direct communication with another source of gas, for example, with a small dead volume.

The tube 200' of FIG. 21 can be selectively opened or closed in the same manner as already described above in reference with the tube 200 of FIGS. 8-20, although the configuration of FIG. 21 introduces some differences. Indeed, in FIG. 21, the inhalation chamber 1' differs from the inhalation chamber 1 of FIGS. 1-7 by displacing the location of the gas opening 10' away from the pMDI opening 12' to shorten the tube 200'. The inhalation chamber 1' and the configuration of the tube 200' therethrough are therefore different in this case, but the tube 200' itself works in a similar manner in terms of possible variants of openings, complimentary shapes forming the tube, and in terms of rotation by the user to selectively open or close the tube 200'.

However, having the tube 200' not completely inside the inhalation chamber 1' gives more possibilities for manipulation by the user. As shown in FIG. 21, the tube 200' can be accessed and handled directly outside the inhalation chamber 1'. The base portion 222' protrudes outside of the inhalation chamber 1' for connection to the source of gas, and does not need to comprise any pMDI receptacle 229.

Therefore, as the base portions 222' and 242' of the tube 200' are accessible, some particularities described above are not necessary: the cone surface 249 starting from the base portion 242, the mating surface 247, and the annular portion 245. These elements can therefore be absent in this embodiment (but they can also be present as an option). The base portion 242', or the base portion 229', can be rotated directly to cause the relative rotation between the parts forming the tube 200', hence the switching between the open and closed states.

Figure 22:
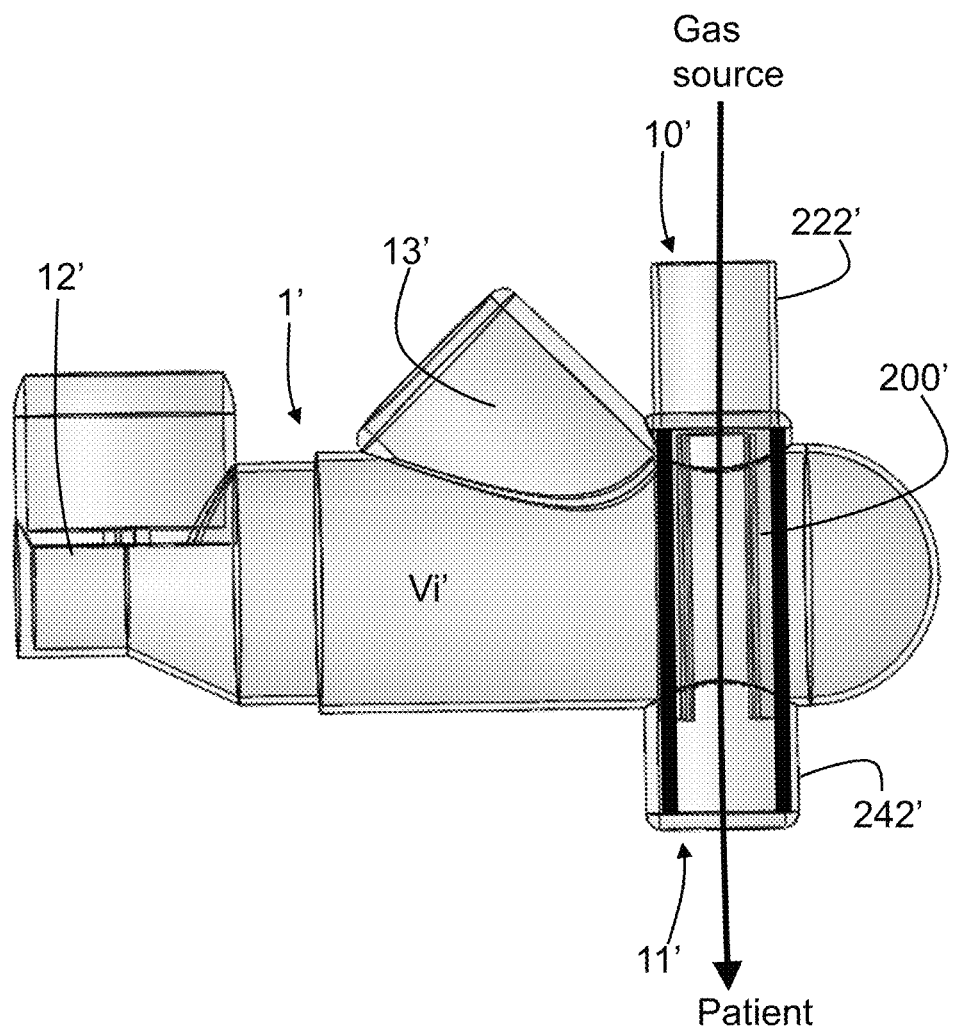
FIG. 22 is a side view illustrating the inhalation chamber of FIG. 21 with a tube therein, in closed position for by-passing the inner volume of the inhalation chamber.

When the tube 200' is used, it can be closed, thereby by-passing the inhalation chamber 1' and providing direct and short communication between the opening 10' to the source of gas and the opening 11' The tube 200' can also be handled either as described above in relation with FIGS. 8-20, or by simple relative rotation of the bases 222 and/or 242 which extend outside the inhalation chamber 1'. When no aerosol is being dispensed in the inhalation chamber 1', the tube 200' will be closed to bypass the inhalation chamber 1' and minimize the dead volume of the respiratory circuit, as shown in FIG. 22.

Figure 23:
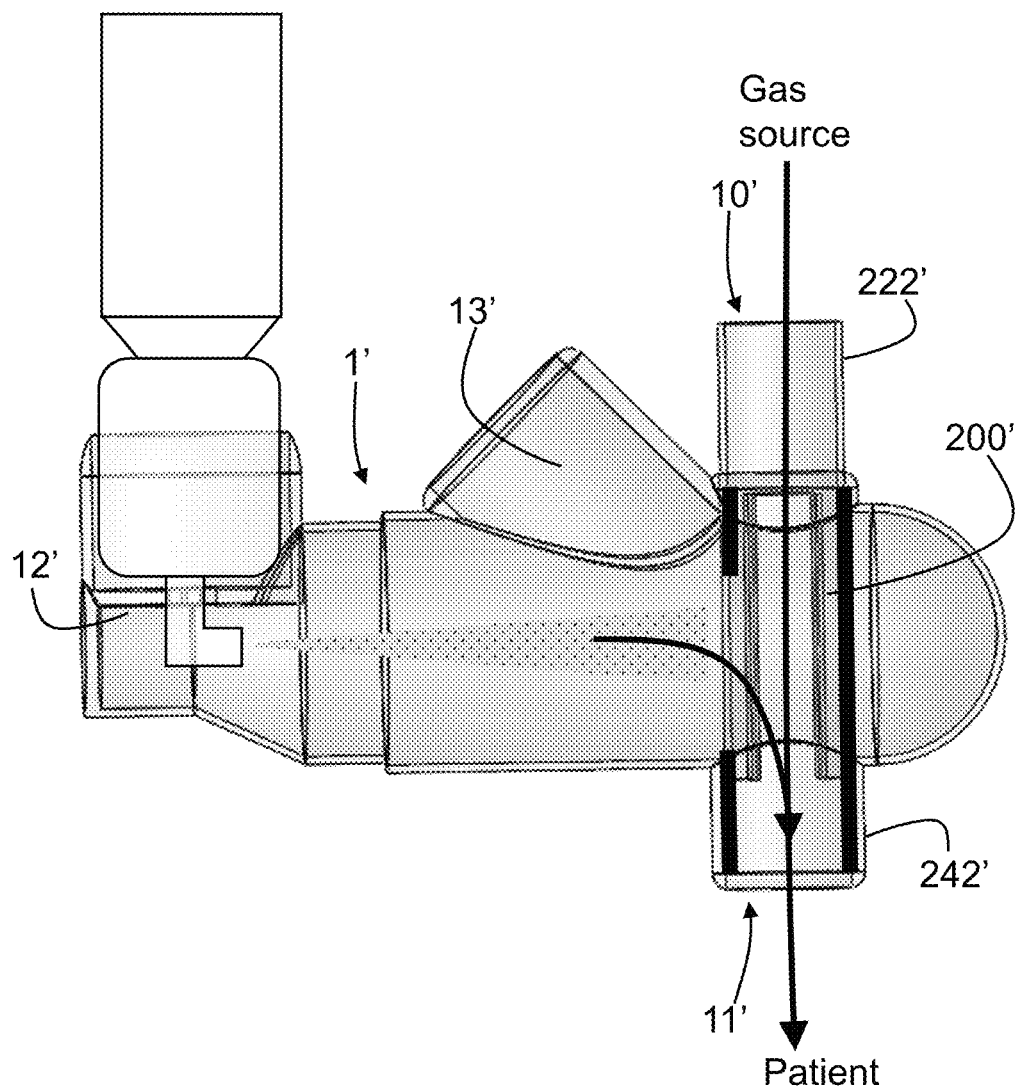
FIG. 23 is a side view illustrating the inhalation chamber of FIG. 21 with a tube therein, in open position for administering aerosol from a metered-dose inhaler.
Figure 24:
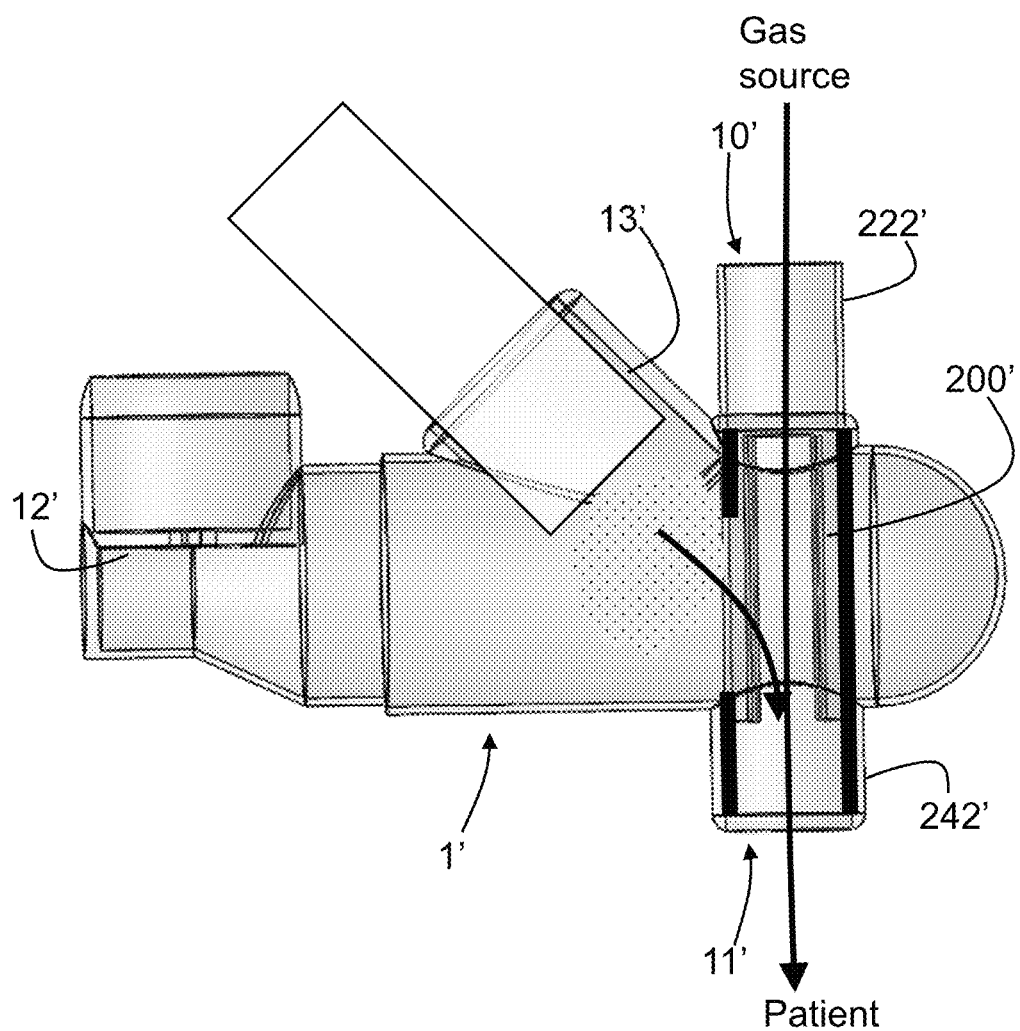
FIG. 24 is a side view illustrating the inhalation chamber of FIG. 21 with a tube therein, in open position for administering aerosol from a nebulizer.

When the tube 200' is opened, there is fluid communication between the inner volume Vi' of the inhalation chamber and the inside of the tube 200'. In this embodiment, the pMDI opening 12' is not located within the tube 200'. Instead, it is located away from the tube 200, or more specifically, opposite the tube 200' in the inhalation chamber 1'. The nebulizer opening 13' is located in-between, closer to the tube 200'. The tube 200' will be opened, for example by sliding (including rotation or translation, for example), when aerosol is being dispensed. For example, either the pMDI or the nebulizer may be connected in the appropriate port, i.e., openings 12' or 13', respectively, as shown in FIGS. 23-24. Opening the tube 200' therefore allows the administration of aerosol for the treatment of the patient (typically, for deposition of the drug in the patient's lungs). The flux of aerosol is thereby combined to the gas flow from the source of gas, and this combination from the appropriate source of aerosol with the source of gas only happens in the open position.

Typically, the pMDI opening 12' would receive a pMDI comprises an elbow that ejects the aerosol, and therefore, this right-angle elbow ensures that in the configuration of FIG. 23, the jet of aerosol from the pMDI will actually be directed toward the opening window of the tube 200'. The nebulizer is more likely to be ejected in a straight manner, hence the inclination of the nebulizer opening 13' to direct at least partly the jet from the nebulizer toward the opening window of the tube 200', as shown in FIG. 24.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A tube for an inhalation chamber, the tube having a longitudinal axis and comprising:
    a first tube portion having a first base with a cylinder shape and a first half-cylinder portion extending from the first base;
    a second tube portion having a second base with a cylinder shape and a second half-cylinder portion extending from the second base, the second half-cylinder portion being complementary and slidably mating in rotation only with the first half-cylinder portion, the second base being aligned with the first base about the longitudinal axis, the second tube portion being rotatable with respect to the longitudinal axis of the tube to allow the second half-cylinder portion to cover different azimuth angles with respect to the first half-cylinder portion and thereby, upon rotation about the longitudinal axis, open or close the tube between the first base and the second base to form a window opening on an inner volume of the inhalation chamber for receiving aerosol.

2. An inhalation chamber comprising the tube of claim 1 extending between a gas source opening and a patient output opening of the inhalation chamber, the inhalation chamber comprising at least one opening for dispensing aerosol into the tube.

3. The inhalation chamber of claim 2, further comprising at least two openings for dispensing aerosol, one of the at least two openings located away from the tube, the other one of the at least two openings being located between the tube and the one of the at least two openings located away from the tube.

4. The inhalation chamber of claim 3, wherein the one of the at least two openings located away from the tube is an opening for a metered-dose inhaler and the other one of the at least two openings is an opening for a nebulizer.

5. The inhalation chamber of claim 2, further comprising at least two openings for dispensing aerosol, one of the at least two openings located at the gas source opening, one of the at least two openings not located at the gas source opening or at the patient output opening.

6. The inhalation chamber of claim 5, wherein the at least two openings for dispensing aerosol comprise:
    a first opening, not located at the gas source opening or at the patient output opening, for a nebulizer provided by a surface of the inhalation chamber, and
    a second opening, located at the gas source opening, for a metered-dose inhaler, the first base being secured into the gas source opening of the inhalation chamber and having a first base opening aligned with the second opening for the metered-dose inhaler of the inhalation chamber.

7. A duct for an inhalation chamber, the duct extending through an inner volume of the inhalation chamber and comprising:
    a first portion having a half-cylinder shape;
    a second portion having a half-cylinder shape to form a closed duct having a longitudinal axis, the second portion slidably mating with the first portion in rotation about said longitudinal axis;
    the second portion being slidable only in rotation about said longitudinal axis by a user to open the closed duct by forming a window at a surface of the duct, the window opening on the inner volume of the inhalation chamber, the window opening on the inner volume of the inhalation chamber for receiving aerosol.

8. A method for operating an inhalation chamber comprising:
    providing a duct in the inhalation chamber extending from an opening for a source of gas to an opening for patient output, the duct comprising two portions, each having a shape, the shapes being complementary to form the duct, and slidable in relation with each other only in rotation about a longitudinal axis of the duct;
    connecting to the inhalation chamber a first aerosol dispenser at a first aerosol dispenser input on the inhalation chamber; and
    making a relative displacement between the two portions of the duct, only in rotation about a longitudinal axis of the duct to close the duct to by-pass an inner volume of the inhalation chamber; and
    making a relative displacement between the two portions of the duct, only in rotation about the longitudinal axis of the duct, to open the duct by forming a window toward the inner volume of the inhalation chamber facing the first aerosol dispenser input on the inhalation chamber for receiving aerosol from the first aerosol dispenser.

* * * * *